United States Patent

Benes et al.

[11] Patent Number: 5,866,566
[45] Date of Patent: Feb. 2, 1999

[54] DERIVATIVES OF 10, 11-DIHYDRO-10-OXO-5H-DIBENZ/B,F/AZEPINE-5-CARBOXAMIDE

[75] Inventors: Jan Benes; Patricio M.V.A. Soares Da Silva, both of Porto; David Alexander Learmonth, Maia, all of Portugal

[73] Assignee: Portela & Ca., S.A., Porto, Portugal

[21] Appl. No.: 862,196

[22] Filed: May 23, 1997

[30] Foreign Application Priority Data

May 27, 1996 [PT] Portugal ................................. 101.876

[51] Int. Cl.$^6$ ......................... A61K 31/55; C07D 223/28
[52] U.S. Cl. ............................................ 514/217; 540/589
[58] Field of Search ............................. 540/589; 514/217

[56] References Cited

U.S. PATENT DOCUMENTS 4,559,174  12/1985  Aufderhaar ............................... 540/589
5,466,683  11/1995  Sterling ..................................... 540/589

*Primary Examiner*—Mark L. Berch
*Attorney, Agent, or Firm*—Ostrolenk, Faber, Gerb & Soffen, LLP

[57] ABSTRACT

Compounds of general formula I are described

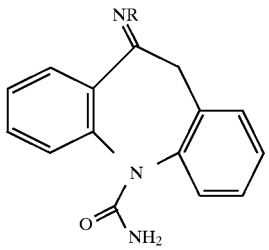

as is a process for their preparation which consists of reacting a compound of formula II

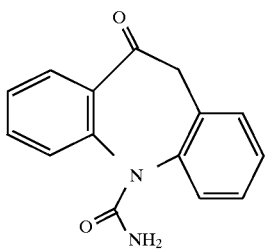

with hydroxylamine or its derivatives of formula III $$H_2NOR^2 \qquad (III)$$

The compounds cited in the present invention have valuable pharmaceutical properties namely in the treatment of some disturbances in the central and peripheral nervous system.

7 Claims, No Drawings

DERIVATIVES OF 10, 11-DIHYDRO-10-OXO-5H-DIBENZ/B,F/AZEPINE-5-CARBOXAMIDE

DESCRIPTION

New Derivatives of 10,11-dihydro-10-oxo-5H-dibenz/b,f/azepine-5-carboxamide

The present invention relates to new derivatives of 10,11-dihydro-10-oxo-5H-dibenz/b,f/azepine-5-carboxamide, to the method of their preparation and to pharmaceutical compositions containing them. The compounds have valuable pharmaceutical properties in the treatment of some central and peripheral nervous system disorders.

10,11-Dihydro-10-oxo-5H-dibenz/b,f/azepine-5-carboxamide (oxcarbazepine) is a well established agent in the management of epilepsy, trigeminal neuralgia and affective disorders (see e.g. Drugs 43(6), 873 (1992)). In some patients however, oxcarbazepine precipitates severe adverse reactions, particularly allergic reactions and it also produces a decrease in serum sodium levels. Another disadvantage of oxcarbazepine is associated with its rapid metabolism; as a consequence, the drug should normally be used in a three times per day regime.

The invention aims to achieve an improvement in some of the above mentioned characteristics and relates to new compounds of general formula I;

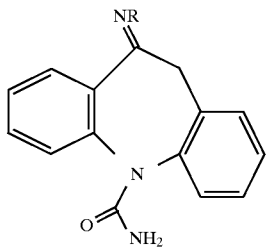

wherein: R is hydroxy, alkyl, cycloalkyl, alkylaryl, alkylcycloalkyl, alkylheteroaryl, benzoyloxy, 3-methoxybenzoyloxy or 2-chlorophenylsemicarbozono or R is the group —O—CO—$R^1$ wherein $R^1$ is hydrogen, alkyl, cycloalkyl, alkylcycloalkyl, alkylaryl, benzyloxy, alkoxy or heteroaryl or R is the group —O—$R^2$ wherein $R^2$ is alkyl, alkylaryl, benzyl or naphthoyl, or R is the group NH$R^3$ wherein $R^3$ is hydrogen, —CO—NH$_2$, —CS—NH$_2$, alkyl, phenyl, dinitrophenyl, alkylaryl, alkylcycloalkyl, alkylcarbonyl or arylcarbonyl; the term alkyl means a carbon chain, straight or branched, containing from one to six carbon atoms, optionally substituted by alkoxy, halogen, alkoxycarbonyl or hydroxycarbonyl groups; the term cycloalkyl represents an alicyclic group with three to six carbon atoms; the term aryl represents a phenyl or naphthyl group optionally substituted by alkoxy, halogen or nitro groups; the term heteroaryl represents a five or six membered aromatic ring incorporating an atom of oxygen, sulphur or nitrogen; and the term halogen represents fluorine, chlorine, bromine or iodine.

Preferred compounds of general formula I include:

1. 10,11-dihydro-10-hydroxyimino-5H-dibenz/b,f/azepine-5-carboxamide
2. 10,11-benzyloxyimino-10,11-dihydro-5H-dibenz/b,f/azepine-5-carboxamide
3. 10-acetyloxyimino-10,11-dihydro-5H-dibenz/b,f/azepine-5-carboxamide
4. 10,11-dihydro-10-propionyloxyimino-5H-dibenz/b,f/azepine-5-carboxamide
5. 10-butyroyloxyimino-10,11-dihydro-5H-dibenz/b,f/azepine-5-carboxamide
6. 10,11-dihydro-10-pivaloyloxyimino-5H-dibenz/b,f/azepine-5-carboxamide
7. 10,11-dihydro-10-[(1-napthoyloxy)imino]-5H-dibenz/b,f/azepine-5-carboxamide
8. 10-benzoyloxyimino-10,11-dihydro-5H-dibenz/b,f/azepine-5-carboxamide
9. 10,11-dihydro-10-succinoyloxyimino-5H-dibenz/b,f/azepine-5-carboxamide
10. 10,11-dihydro-10-glutaroyloxyimino-5H-dibenz/b,f/azepine-5-carboxamide
11. 10,11-dihydro-10-isobutoxycarbonyloxyimino-5H-dibenz/b,f/azepine-5-carboxamide
12. 10,11-dihydro-10-methoxyimino-5H-dibenz/b,f/azepine-5-carboxamide
13. 10,11-dihydro-10-(S)-(-)-camphanoyloxyimino-5H-dibenz/b,f/azepine-5-carboxamide
14. 10,11-dihydro-10-[(3-methoxybenzoyloxyimino)]-5H-dibenz/b,f/azepine-5-carboxamide
15. 10,11-dihydro-10-nicotinoyloxyimino-5H-dibenz/b,f/azepine-5-carboxamide
16. 10,11-dihydro-10-ethoxycarbonyloxyimino-5H-dibenz/b,f/azepine-5-carboxamide
17. 10-butoxycarbonyloxyimino-10,11-dihydro-5H-dibenz/b,f/azepine-5-carboxamide
18. 10-benzyloxycarbonyloxyimino-10,11-dihydro-5H-dibenz/b,f/azepine-5-carboxamide
19. 10,11-dihydro-10-phenylhydrazono-5H-dibenz/b,f/azepine-5-carboxamide
20. 10,11-dihydro-10-hydrazono-5H-dibenz/b,f/azepine-5-carboxamide
21. 10,11-dihydro-10-(2,4-dinitrophenylhydrazono)-5H-dibenz/b,f/azepine-5-carboxamide
22. 10,11-dihydro-10-semicarbozono-5H-dibenz/b,f/azepine-5-carboxamide
23. 10,11-dihydro-10-thiosemicarbozono-5H-dibenz/b,f/azepine-5-carboxamide
24. 10-(2-chlorophenylsemicarbozono)-5H-dibenz/b,f/azepine-5-carboxamide
25. 10,11-dihydro-10-methoxycarbonylpropylimino-5H-dibenz/b,f/azepine-5-carboxamide Another aspect of the invention relates to the method of preparation of compounds of formula I where substituent R is defined above, by reacting the compound of formula II

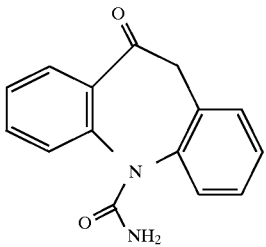

with hydroxylamine or its derivatives of formula III

wherein substituent $R^2$ is defined above, or by reaction of a compound of formula II with semicarbazide, thiosemicarbazide or derivatives of hydrazine of formula IV

wherein substituents $R^3$ and $R^4$ are defined above, or by reacting the compound of formula V

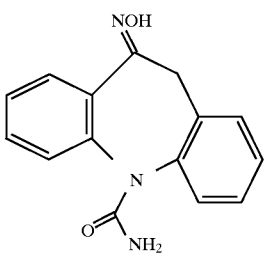

with acylating reagents of formula VI $$A-CO-R^1 \quad \quad VI$$

Wherein $R^1$ is the same as defined for general formula I; A is hydroxy, halogen or —O—CO—R' or —O—CO—OR', wherein R' is lower alkyl (C1 to C4), or by reacting the compound of formula V with acylating reagents of formula VII $$Cl-CO-OR^1 \quad \quad VII$$

wherein $R^1$ is the same as defined for general formula I; the acylation reaction can be carried out in the presence of condensing agents which include dicyclohexylcarbodiimide, carbonyldiimidazole, ethyl or isobutylchloroformate and/or in the presence of organic or inorganic bases such as for example, pyridine, triethylamine or alkalic bicarbonates in inert solvents such as hydrocarbons, chlorinated alkanes, ethers or aprotic dipolar solvents or the reaction can be run in a mixture of the above mentioned solvents or in the absence of any solvent.

Reactions as described above may be performed at various temperatures and pressures, e.g. between 0° C. and the boiling temperature of the reaction mixture at the pressure used.

Compound II is known (see e.g. German Patent 2 001 087) and compounds of formulae III, IV, VI and VII can be made by those skilled in the art by methods described for example in the book "Comprehensive Organic Transformations" by R. C. Larock, VCH Publishers, 1989.

Still another aspect of the invention comprises a method of making pharmaceutical compositions consisting of mixing a compound of formula I with a pharmaceutically acceptable carrier.

The use of some compounds of formula I may be useful in the treatment of epilepsy, trigeminal neuralgia and affective cerebral disorders and alterations of the nervous function in degenerative and post-ischaemic diseases.

Epilepsy is one of the most common afflictions of man with a prevalence of approximately 1%. Since the time of Hughlings Jakson more than 100 years ago, epileptic seizures have been known to represent "occasional, sudden, excessive, rapid and local discharges of nerve tissue". Epileptic seizures are divided fundamentally into two groups: partial and generalised. Partial seizures are those in which the discharge begins locally, and often remains localised. Generalised seizures involve the whole brain, including the reticular system, thus producing abnormal electrical activity throughout both hemispheres and immediate loss of consciousness. Partial seizures are divided in: (a) partial simple seizures, (b) complex partial seizures and (c) partial seizures secondarily generalised. The generalised seizures include: (1) tonic-clonic seizures (grand mal), (2) absence seizures (petit mal), (3) myoclonic seizures, (4) atonic seizures, (5) clonic seizures and (6) tonic seizures. Epilepsy, in contradistinction to seizures, is a chronic disorder characterised by recurrent seizures (Gastaut, H.: Dictionary of epilepsy. World Health Organization, Geneve, 1973).

There are two ways in which drugs might abolish or attenuate seizures: (a) through effects on altered neurones of seizure foci to prevent or reduce their excessive discharge, and (b) through effects that would reduce the spread of excitation from seizure foci and prevent disruption of function of normal aggregates of neurones. The majority, if not all, of the available antiepileptic drugs work at least by the second mechanism, since all modify the ability of the brain to respond to various seizure-evoking stimuli. Convulsant drugs, such as pentylenetetrazol (metrazol) are often used, particularly in the testing of anticonvulsant agents, and seizures caused by electrical stimulation of the whole brain are used for the same purpose. It has been found empirically that activity in inhibiting metrazol-induced seizures and in raising the threshold for production of electrically induced seizures is a fairly good index of effectiveness against absence seizures. On the other hand, activity in reducing the duration and spread of electrically induced convulsions correlates with effectiveness in controlling other types of epilepsy, such as tonic-clonic seizures.

The anticonvulsant effect of compounds of formulae I was studied in a model of electrically induced convulsions, the maximal electroshock (MES) test, and in a model of chemical induced convulsions, the metrazol test. The MES test allows the evaluation of the ability of drugs to prevent electrically induced tonic hindlimb extension in rats, the efficacy of which is thought to be predictive of anticonvulsant efficacy against generalised tonic-clonic seizures in man (grand mal). The metrazol test predicts the ability of potential antiepileptic agents to prevent clonic seizures and to be effective against absence seizures (petit mal).

Materials and Methods

Male Wistar rats obtained from the animal house of the Harlan Interfauna Ibérica (Barcelona, Spain) and weighing 180 to 280 g were used. Animals were kept two per cage under controlled environmental conditions (12 hr light/dark cycle and room temperature 24   C). Food and tap water were allowed ad libitum and the experiments were all carried out during daylight hours.

1—MES Test

MES stimulation was applied for 0.2 s, using a Ugo Basile ECT unit 7801, with a frequency of 100 Hz, pulse width of 0.6 ms and a current of 150 mA through bipolar corneal electrodes. A drop of electrolyte/anaesthetic, oxibuprocaine chloride, was applied in the eyes of all animals immediately before placement of corneal electrodes. Abolition of the hindleg tonic extensor component, was used as the endpoint. These experimental conditions produced tonic-clonic convulsions in 97% of animals tested and only rats showing typical tonic-clonic convulsions were used. All rats were submitted to a maximum of 3 MES sessions: the first MES session was performed to screen the animals and select those rats presenting a typical convulsive behaviour. The day after, rats were given the compounds to be tested or the vehicle and submitted to a second MES session 2 or 4 hours after the administration of test drugs. The third MES session was performed at 6, 8 or 12 hours after the administration of test drugs. The time interval between each MES session was at least 4 hours (rats tested at 2 hours were retested at 6 hours and rats tested at 4 hours were retested at 8 hours). The evaluation of the anticonvulsive profile of test drugs was based on the duration of the tonic phase (in seconds) being each rat its own control (internal control) as obtained in the first MES session. An external control group was also studied; in this particular case, rats were given the vehicle and submitted to the three MES sessions procedure, as described above. All drugs used were suspended in 0.5% carboxymethylcellulose (4 ml/kg) and given by stomach tube.

2—Metrazol Test

Administration of compounds of formula I was performed 2 hours before the administration of metrazol. Metrazol (75 mg/kg) was given subcutaneously in the back; this dose of metrazol was found to produce convulsions in 95% of the animals. The parameters observed concern the duration of seizures in a 30 minute observation period following the administration of metrazol. $ED_{50}$(mg/kg) is the dose giving 50% reduction of duration of the seizure.

Results

1—MES Test

At the highest dose tested (30 mg/kg), compounds of formula I produced a complete protection against MES after 2 hours of administration. At 4 and 8 hours the protection conferred by compounds of formula I was similar to that produced by the reference compound carbamazepine. At the highest dose tested (30 mg/kg), carbamazepine produced a complete protection against MES after 2 hours of administration; at 4 and 8 hours after administration the protection conferred was still above 80%. The $ED_{50}$ values for carbamazepine at 2, 4 and 8 hours after the administration was 5.6, 11.3 and 20.6. mg/kg, respectively. The $ED_{50}$ values for compounds of formula I at 2, 4 and 8 hours after the administration were 6.9, 19.8 and 18.9 mg/kg, respectively. Oxcarbazepine performed not so potently as did carbamazepine and compounds of formula I. The $ED_{50}$ values for oxcarbazepine at 2, 4 and 8 hours after the administration were 9.7, 20.2 and 22.3 mg/kg, respectively.

2—Metrazol Test

Compounds of formula I were effective in protecting rats against convulsions induced by metrazol. The highest effective dose of compounds of formula I was 30 mg/kg and reduced the total seizure time by 44%. Carbamazepine at 30 and 60 mg/kg produced a 41% and 44%, respectively, decrease in total seizure time. Oxcarbazepine performed less potently than did carbamazepine. At 30 and 60 mg/kg oxcarbazepine a 3% and 32% decrease in total seizure time was observed, respectively.

Conclusion

Compounds of formula I possess valuable antiepileptic activity as screened in the MES and metrazol tests and are endowed with greater or similar anticonvulsant potency to that of reference compounds carbamazepine or oxcarbazepine.

The utilisation of compounds of formula I may prove useful in man for the treatment of some other central and peripheral nervous system disorders, e.g. for trigeminal neuralgia and brain affective disorders nervous function alterations in degenerative and post-ischemic diseases.

For the preparation of pharmaceutical compositions from the compounds of formula I, inert pharmaceutically acceptable carriers are admixed with the active compounds. The pharmaceutically acceptable carriers may be either solid or liquid. Solid form preparations include powders, tablets, dispersible granules and capsules. A solid carrier can be one or more substances which may also act as diluents, flavouring agents, solubilizers, lubricants, suspending agents, binders or tablet disintegrating agents; it may also be an encapsulating material.

Preferably, the pharmaceutical preparation is in unit dosage form, e.g. packaged preparation, the package containing discrete quantities of preparation such as packed tablets, capsules and powders in vials or ampoules.

The dosages may be varied depending on the requirement of the patient, the severity of the disease and the particular compound being employed. For convenience, the total daily dosage may be divided and administered in portions throughout the day. Determination of the proper dosage for a particular situation is within the skill of those in the medical art.

The invention disclosed herein is exemplified by the following examples of preparation which should not be construed to limit the scope of the disclosure. Alternative pathways and analogous structures may be apparent to those skilled in the art.

EXAMPLES

Example 1

10,11-dihydro-10-hydroxyimino-5H-dibenz[b,f]azepine-5-carboxamide

A suspension of 4.0 g (15.86 mmol) of 10,11-dihydro-10-oxo-5H-dibenz[b,f]azepine-5-carboxamide and 3.86 g (55.49 mmol) of hydroxylamine hydrochloride in 100 mL of absolute alcohol was treated with 3.76 g (47.57 mmol) of pyridine. The mixture was heated at reflux for 1 hour and then the ethanol was removed by evaporation under reduced pressure. The residue was partitioned between 150 mL of water and 150 mL of dichloromethane. The organic layer was separated and washed with 50 mL of 1M aqueous HCl, a saturated solution of $NaHCO_3$ and brine, then dried by sodium sulphate. Filtration and evaporation of the solvent under reduced pressure gave an off-white solid which was triturated with hot ethanol to give the desired compound as a white powder of m.p. 230.4° to 231.5° C.

Example 2

Using a similar procedure to that described in the preceding example but employing the appropriate hydroxylamine, 10-benzyloxyimino-10,11-dihydro-5H-dibenz[b,f]azepine-5-carboxamide was prepared.

Example 3

10-acetyloxyimino-10,11-dihydro-5H-dibenz[b,f]azepine-5-carboxamide

A suspension of 0.5 g (1.87 mmol) of 10,11-dihydro-10-hydroxyimino-5H-dibenz[b,f]azepine-5-carboxamide in 25 mL of dichloromethane and 0.72 g (9.16 mmol) of pyridine was treated with 0.57 g (5.61 mmol) of acetic anhydride. The resulting mixture was stirred at room temperature overnight and then diluted with 10 mL of dichloromethane. The organic phase was extracted with 20 mL of 1M aqueous HCl, a saturated solution of $NaHCO_3$ and brine, then dried by sodium sulphate. The solvent was then removed by evaporation under reduced pressure and the crude product was crystallised from a mixture of dichloromethane and ethyl acetate to give the desired product as white crystals of m.p. 175.8°–176.9° C.

Example 4–11

By the application of the above described technique but using the appropriate anhydrides, the following compounds were prepared:

10,11-dihydro-10-propionyloxyimino-5H-dibenz[b,f]azepine-5-carboxamide 10-butyroyloxyimino-10,11-dihydro-5H-dibenz[b,f]azepine-5-carboxamide 10,11-dihydro-10-pivaloyloxyimino-5H-dibenz[b,f]azepine-5-carboxamide 10,11-dihydro-10-[(1-naphthoyloxy)imino]-5H-dibenz[b,f]azepine-5-carboxamide 10-benzoyloxyimino-10,11-dihydro-5H-dibenz[b,f]
azepine-5-carboxamide 10,11-dihydro-10-succinoyloxyimino-5H-dibenz[b,f]
azepine-5-carboxamide 10,11-dihydro-10-glutaroyloxyimino-5H-dibenz[b,f]
azepine-5-carboxamide 10,11-dihydro-10-isobutoxycarbonyloxyimino-5H-dibenz
[b,f]azepine-5-carboxamide

Example 12

10,11-dihydro-10-methoxyimino-5H-dibenz[b,f]
azepine-5-carboxamide

To a suspension of 0.2 g (0.75 mmol) of 10,11-dihydro-10-hydroxyimino-5H-dibenz[b,f]azepine-5-carboxamide in 2 mL of acetone cooled to 0° C. was added a solution of 0.065 g (1.16 mmol) of potassium hydroxide in 1 mL of water followed by 0.164 g (1.16 mmol) of iodomethane. The resulting mixture was stirred at room temperature overnight then 10 mL of water was added. The mixture was extracted with ether and the organic layer was washed with water and brine, then dried by sodium sulphate and filtered. The solvent was removed by evaporation under reduced pressure and the residue chromatographed on silica gel with a 3% methanol-dichloromethane mixture. Chromatographically homogenous fractions were pooled, the solvents were removed under reduced pressure and the residue was crystallised from toluene to give the product as off-white crystals of m.p. 157.9°–159.4° C.

Example 13

10,11-dihydro-10-(S)-(-)-camphanoyloxyimino-5H-dibenz[b,f]azepine-5-carboxamide

To a suspension of 0.15 g (0.56 mmol) of 10,11-dihydro-10-hydroxyimino-5H-dibenz[b,f]azepine-5-carboxamide and 0.01 g (0.08 mmol) of 4-dimethylaminopyridine in 5 mL of dichloromethane and 0.22 g (2.8 mmol) of pyridine was added 0.15 g (0.67 mmol) of (S)-(-)-camphanic chloride in portions. The resulting mixture was stirred for 2 hours at room temperature whereupon a further portion of 0.1 g, (0.46 mmol) of (S)-(-)-camphanic chloride was added. After stirring for a further 1.5 hours, 5 mL of dichloromethane followed by 5 mL of ice-water was added. The organic layer was separated and washed with 10 mL of 2M aqueous HCl, a saturated solution of NaHCO₃ and brine, then dried by sodium sulphate and filtered. The solvent was removed by evaporation under reduced pressure and the residue triturated with ether to give an off-white solid which was crystallised from a mixture of dichloromethane and ethyl acetate to give the desired product as white crystals of m.p. 187° to 187.9° C.

Example 14–15

By the application of the above described technique but using the appropriate acid halogenides, the following compounds were prepared:

10,11-dihydro-10-[(3-methoxybenzoyloxy)imino]-5H-dibenz[b,f]azepine-5-carboxamide 10,11-dihydro-10-nicotinoyloxyimino-5H-dibenz[b,f]
azepine-5-carboxamide

Example 16

10,11-dihydro-10-ethoxycarbonyloxyimino-5H-dibenz[b,f]azepine-5-carboxamide

To a suspension of 0.2 g (0.74 mmol) of 10,11-dihydro-10-hydroxyimino-5H-dibenz[b,f]azepine-5-carboxamide and 0.01 g (0.08 mmol) of 4-dimethylaminopyridine in 10 mL of dichloromethane and 0.29 g (3.7 mmol) of pyridine was added 0.28 g (2.6 mmol) of ethyl chloroformate dropwise. The resulting mixture was stirred at room temperature for 2 hours whereupon it was extracted with 20 mL of 1M aqueous HCl and a saturated solution of NaHCO₃, then dried by sodium sulphate and filtered. The solvent was removed by evaporation under reduced pressure and the residue was crystallised from a mixture of dichloromethane and ethyl acetate to give white crystals of m.p. 188.9°–190° C.

Example 17–18

By the application of the above described technique but using the appropriate chloroformates, the following compounds were prepared:

10-butoxycarbonyloxyimino-10,11-dihydro-5H-dibenz[b,f]
azepine-5-carboxamide 10-benzyloxycarbonyloxyimino-10,11-dihydro-5H-dibenz
[b,f]azepine-5-carboxamide

Example 19

10,11-dihydro-10-phenylhydrazono-5H-dibenz[b,f]
azepine-5-carboxamide

A mixture of 0.2 g (0.8 mmol) of 10,11-dihydro-10-oxo-5H-dibenz[b,f]azepine-5-carboxamide, 0.5 g (4.6 mmol) of phenylhydrazine and 0.5 g (6 mmol) of sodium acetate in a mixture of 5 mL of water, 5 mL of ethanol and 3 drops of concentrated hydrochloric acid was heated at 60° C. for thirty minutes and then allowed to cool to room temperature. The precipitate was then filtered and washed with cold water and dilute ethanol to give the desired product as yellow crystals of m.p. 220° to 220.8° C.

Example 20–21

By the application of the above described technique but using the appropriate hydrazines, the following compounds were prepared:

10,11-dihydro-10-hydrazono-5H-dibenz[b,f]azepine-5-carboxamide 10,11-dihydro-10-(2,4-dinitrophenylhydrazono)-5H-dibenz
[b,f]azepine-5-carboxamide

Example 22

10,11-dihydro-10-semicarbozono-5H-dibenz[b,f]
azepine-5-carboxamide

To a stirred solution of 0.4 g (3.59 mmol) of semicarbazide hydrochloride and 0.6 g (7.32 mmol) of sodium acetate in 4 mL of water was added 0.2 g (0.8 mmol) of 10,11-dihydro-10-oxo-5H-dibenz[b,f]azepine-5-carboxamide. The resulting suspension was warmed on a water bath and 6 mL of ethanol was added until a solution was obtained. The solution was heated at 60° C. for 1.5 hours and then cooled to room temperature. The ethanol was removed by evaporation under reduced pressure and the the residue cooled to 5° C. for 2 hours. The crystalline precipitate was filtered and washed with cold water to give the desired product as pale yellow crystals of m.p. 247.2°–248.6° C.

Example 23–24

By the application of the above described technique but using the appropriate semicarbazides, the following compounds were prepared:

10,11-dihydro-10-thiosemicarbozono-5H-dibenz[b,f]
azepine-5-carboxamide 10-(2-chlorophenylsemicarbozono)-10,11-dihydro-5H-
dibenz[b,f]azepine-5-carboxamide Example 25

10,11-dihydro-10-methoxycarbonylpropylimino-5H-
dibenz[b,f]azepine-5-carboxamide To a suspension of 0.2 g (0.79 mmol) of 10,11-dihydro-10-oxo-5H-dibenz[b,f]azepine-5-carboxamide and 0.1 g (0.67 mmol) of methyl-4-aminobutyrate hydrochloride in 5 mL of xylene was added 0.07 g (0.49 mmol) of boron trifluoride diethyl etherate. The resulting mixture was heated at 135° C. for seven hours and then allowed to cool to room temperature. The mixture was then filtered and the residue was extracted with toluene. The combined extracts were evaporated under reduced pressure and the residue chromatographed on silica gel using a 4:1 mixture of petroleum ether-ethyl acetate. Chromatographically homogenous fractions were pooled and the solvents were removed under reduced pressure to give the desired product as a yellow oil which crystallised on standing to give yellow crystals which decomposed on heating without melting.

We claim:

1. Compound of formula I

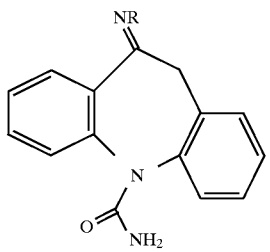

I wherein: R is hydroxy, alkyl, cycloalkyl, alkylaryl, alkylcycloalkyl, alkylheteroaryl benzoyloxy, 3-methoxybenzoyloxy or 2-chlorophenylsemicarbozono or R is the group —O—CO—$R^1$ wherein $R^1$ is hydrogen, alkyl, cycloalkyl, alkylcycloalkyl, alkylaryl, benzyloxy, alkoxy or heteroaryl or R is the group —O—$R^2$ wherein $R^2$ is alkyl, alkylaryl, benzyl or naphthoyl, or R is the group $NHR^3$ wherein $R^3$ is hydrogen, —CO—$NH_2$, —CS—$NH_2$, alkyl, phenyl, dinitrophenyl, alkylaryl, alkylcycloalkyl, alkylcarbonyl or arylcarbonyl; the term alkyl means a carbon chain, straight or branched, containing from one to six carbon atoms, optionally substituted by alkoxy, halogen, alkoxycarbonyl or hydroxycarbonyl groups; the term cycloalkyl represents an alicyclic group with three to six carbon atoms; the term aryl represents a phenyl or naphthyl group optionally substituted by alkoxy, halogen or nitro groups; the term heteroaryl represents a five or six membered aromatic ring incorporating an atom of oxygen, sulphur or nitrogen; and the term halogen represents fluorine, chlorine, bromine or iodine.

2. A compound as defined in claim 1 which is:

(1) 10,11-dihydro-10-hydroxyimino-5H-dibenz/b,f/azepine-5-carboxamide (2) 10-benzyloxyimino-10,11-dihydro-5H-dibenz/b,f/azepine-5-carboxamide (3) 10-acetyloxyimino-10,11-dihydro-5H-dibenz/b,f/azepine-5-carboxamide (4) 10,11-dihydro-10-propionyloxyimino-5H-dibenz/b,f/azepine-5-carboxamide (5) 10-butyroyloxyimino-10,11-dihydro-5H-dibenz/b,f/azepine-5-carboxamide (6) 10,11-dihydro-10-pivaloyloxyimino-5H-dibenz/b,f/azepine-5-carboxamide (7) 10,11-dihydro-10-[(1-naphthoyloxyimino)]-5H-dibenz/b,f/azepine-5-carboxamide (8) 10-benzoyloxyimino-10,11-dihydro-5H-dibenz/b,f/azepine-5-carboxamide (9) 10,11-dihydro-10-succinoyloxy-5H-dibenz/b,f/azepine-5-carboxamide

(10) 10,11-dihydro-10-glutaroyloxyimino-5H-dibenz/b,f/azepine-5-carboxamide

(11) 10,11-dihydro-10-isobutoxycarbonyloxyimino-5H-dibenz/b,f/azepine-5-carboxamide

(12) 10,11-dihydro-10-methoxyimino-5H-dibenz/b,f/azepine-5-carboxamide

(13) 10,11-dihydro-10-[(3-methoxybenzoyloxy)imino]-5H-dibenz/b,f/azepine-5-carboxamide

(14) 10,11-dihydro-10-nicotinoyloxyimino-5H-dibenz/b,f/azepine-5-carboxamide

(15) 10,11-dihydro-10-ethoxycarbonyloxyimino-5H-dibenz/b,f/azepine-5-carboxamide

(16) 10-butoxycarbonyloxyimino-10,11-dihydro-5H-dibenz/b,f/azepine-5-carboxamide

(17) 10-benzyloxycarbonyloxyimino-10,11-dihydro-5H-dibenz/b,f/azepine-5-carboxamide

(18) 10,11-dihydro-10-phenylhydrazono-5H-dibenz/b,f/azepine-5-carboxamide

(19) 10,11-dihydro-10-hydrazono-5H-dibenz/b,f/azepine-5-carboxamide

(20) 10,11-dihydro-10-(2,4-dinitrophenylhydrazono)-5H-dibenz/b,f/azepine-5-carboxamide

(21) 10,11-dihydro-10-semicarbozono-5H-dibenz/b,f/azepine-5-carboxamide

(22) 10,11-dihydro-10-thiosemicarbozono-5H-dibenz/b,f/azepine-5-carboxamide

(23) 10-(2-chlorophenylsemicarbozono)-5H-dibenz/b,f/azepine-5-carboxamide

(24) 10,11-dihydro-10-ethoxycarbonylpropylimino-5H-dibenz/b,f/azepine-5-carboxamide.

3. A process for producing at least one compound having the formula I

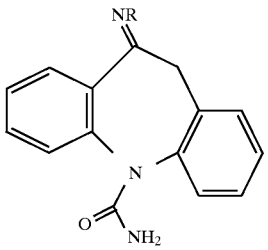

I wherein: R is hydroxy, the group —O—$R^2$ wherein $R^2$ is an alkyl, alkylaryl benzyl or naphthoyl group, or the group $NHR^3$ wherein $R^3$ is hydrogen, —CO—$NH_2$, —CS—$NH_2$, alkyl, phenyl, dinitrophenyl, alkylcycloalkyl, alkylaryl, alkylcarbonyl or arylcarbonyl; the term alkyl means a carbon chain, straight or branched, containing from one to six carbon atoms optionally substituted by alkoxy, halogen, alkoxycarbonyl or hydroxycarbonyl groups; the term cycloalkyl represents an alicyclic group with three to six carbon atoms; the term aryl represents a phenyl or naphthyl group optionally substituted by alkoxy, halogen or nitro groups; the term heteroaryl represents a five or six membered aromatic ring incorporating an atom of oxygen, sulphur or nitrogen; and the term halogen represents fluorine, chlorine, bromine or iodine, by reacting the compound of formula II

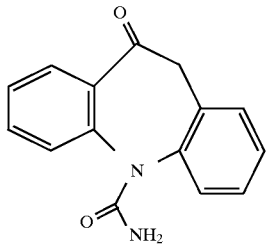

with hydroxylamine or its derivatives of formula III

wherein substituent $R^2$ is defined above, or by reacting a compound of formula II with semicarbazide, thiosemicarbazide or derivatives of hydrazine of formula IV

wherein $R^3$ is defined above, or by reacting a compound of formula V

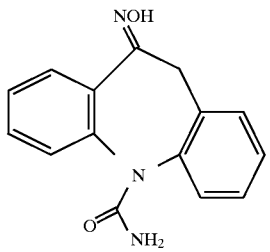

with acylating reagents of formula VI $$A\text{-}CO\text{-}R^1 \qquad (VI)$$

wherein $R^1$ is the same as defined for general formula I; A is hydroxy, halogen or —O—CO—$R^1$ or —O—CO—OR' wherein R' is lower alkyl (C1 to C4), or by reacting the compound of formula V with acylating reagents of formula VII $$Cl\text{—}CO\text{—}OR^1 \qquad (VII)$$

wherein $R^1$ is the same as defined for general formula I.

4. The process as defined in claim 3 wherein the reaction is conducted in the presence of condensing agents and/or bases.

5. A pharmaceutical composition useful in the treatment of central and peripheral nervous system disorders, in the treatment of epilepsy, trigeminal neuralgia, affective brain disorders and nervous function alterations in degenerative and postischaemic diseases, comprising a compound of formula I of claim 1 and a pharmaceutically acceptable carrier.

6. A method for making a pharmaceutical composition comprising of mixing a compound of formula I of claim 1 with a pharmaceutically acceptable carrier.

7. A pharmaceutical composition useful in the treatment of central and peripheral nervous system disorders, in the treatment of epilepsy, trigeminal neuralgia, affective brain disorders and nervous function alterations in degenerative and postischaemic diseases, comprising a compound of claim 2 and a pharmaceutically acceptable carrier.

* * * * *